United States Patent [19]

Hamilton, Jr. et al.

[11] Patent Number: 4,895,997
[45] Date of Patent: Jan. 23, 1990

[54] OLEFIN ISOMERIZATION PROCESS

[75] Inventors: David M. Hamilton, Jr., Houston; Richard A. Kemp, Stafford, both of Tex.

[73] Assignee: Shell Oil Company, Houston, Tex.

[21] Appl. No.: 238,389

[22] Filed: Aug. 31, 1988

[51] Int. Cl.$^4$ .......................... C07C 2/02; C07C 5/23
[52] U.S. Cl. .................................. 585/329; 585/518; 585/643; 585/670; 502/327
[58] Field of Search ............... 585/329, 670, 518, 643; 502/327

[56] References Cited

U.S. PATENT DOCUMENTS

| Re. 28,137 | 8/1974 | Turner et al. | 260/683 D |
|---|---|---|---|
| 2,699,457 | 1/1955 | Ziegler et al. | 260/683.15 |
| 3,310,600 | 3/1967 | Ziegler et al. | 260/683.15 |
| 3,478,124 | 11/1966 | Fernald et al. | 260/683.15 |
| 3,482,000 | 12/1969 | Fernald et al. | 260/683.15 |
| 3,647,906 | 3/1972 | Farley | 260/683 |
| 4,016,245 | 4/1977 | Plank et al. | 423/328 |
| 4,018,845 | 4/1977 | Rausch | 585/670 |
| 4,217,240 | 8/1980 | Bergna | 252/313 |
| 4,257,804 | 3/1981 | Arndt et al. | 71/106 |
| 4,272,409 | 6/1981 | Bergna | 252/455 R |
| 4,293,728 | 10/1981 | Montgomery | 585/670 |
| 4,343,692 | 8/1982 | Winquist | 208/111 |
| 4,451,572 | 5/1984 | Cody | 502/62 |
| 4,727,203 | 2/1988 | Hamilton | 585/329 |

Primary Examiner—Curtis R. Davis
Attorney, Agent, or Firm—Pamela J. McCollough

[57] ABSTRACT

The disclosure of the invention relates to a process for double bond isomerization in which the double bond of an alpha olefinic molecule is moved from the alpha position to an internal position of the olefinic molecule. The catalyst utilized for this migration is a catalyst prepared by incorporating palladium into an alumina hydrogel.

32 Claims, 1 Drawing Sheet

OLEFIN ISOMERIZATION PROCESS

FIELD OF THE INVENTION

This invention relates to a process for the isomerization of olefinic hydrocarbons utilizing a hydrogel-derived catalyst.

BACKGROUND OF THE INVENTION

Long chain linear alpha olefins are hydrocarbons which are always in demand in the chemical industry. Such linear alpha olefins can be converted to corresponding alcohols or aldehydes by conventional "OXO" or hydroformylation processes. Resultant $C_{14}$ to $C_{20}$ alcohols can further be ethoxylated with ethylene or propylene oxide in the presence of a catalyst to form conventional detergents while lower molecular weight alcohols can be esterified with polyhydrate alcohols to form plasticizers of polyvinyl chloride. Also, long chain linear olefins can be converted to alpha olefin sulfonates by treatment with sulfur trioxide and then used as biodegradable detergents.

It is advantageous to formulate higher olefins as a feed material to such processes as hydroformylation from a lower olefin, such ethylene or butylene. It is also desirable to maximize the specific range of carbon atoms present in the end product. For purposes of utility, it is desirable to acquire the maximum quantity of $C_{12}$ to $C_{18}$ alpha olefins starting from ethylene.

A basic process for preparing high molecular weight alpha olefins from ethylene is disclosed in U.S. Pat. No. 3,647,906. This process discloses the combinative treatment of oligomerization of ethylene followed by requisite separation, then isomerization and disproportion of light olefins and heavy olefins derived from the separation zone. In this manner, the specific carbon range of alpha olefins is maximized and the refiners profit margin is greatly increased. All of the specific teachings of this patent are herein incorporated by reference. In the procedure where alpha olefins are isomerized to internal olefins, a catalyst is employed which preferably has little or no polymerization or cracking activity. Suitable examples are exemplified as phosphoric acid, bauxite, alumina supported cobalt oxide, iron oxide or manganese.

A variety of catalysts have been employed for conducting isomerization reactions, such as those disclosed in Reissue U.S. Pat. No. 28,137, U.S. Pat. No. 4,217,240, U.S. Pat. No. 4,257,804, U.S. Pat. No. 4,272,409, U.S. Pat. No. 4,016,245, U.S. Pat. No. 4,343,692, U.S. Pat. No. 4,451,572 and U.S. Pat. No. 4,727,203.

The catalysts in the above references are generally prepared according to conventional methods such as impregnation, wherein a carrier is impregnated with a solution of metals; co-precipitation, wherein a carrier compound and metals are simultaneously precipitated; or co-mulling, wherein dry powders are mixed with a suitable extrusion aid such as water and extruded.

SUMMARY OF THE INVENTION

The present invention relates to a process for the isomerization of olefinic hydrocarbons which comprises contacting said olefinic hydrocarbons with a catalyst prepared by incorporating palladium into an alumina hydrogel and then processing to prepare the catalyst. As used herein, the term "alumina hydrogel" refers to a precipitated aluminum compound in an undried state which has generally been washed free of salts resulting from precipitation. Water is an integral part and major component, typically about 65–95%, of the alumina hydrogel.

It has been found that a hydrogel-derived palladium catalyst shows diminished dimerization reactions in an olefin isomerization reaction when compared to a conventionally prepared catalyst useful for isomerization. The hydrogel catalyst in this invention can be prepared by adding palladium to an alumina hydrogel as a dry salt, a solution, or a mixture of a dry salt and a solution. In an olefin production process combining the steps of oligomerization, isomerization and disproportionation such as that disclosed in U.S. Pat. No. 3,726,938, issued to Berger, it is preferred to use a catalyst prepared according to the instant invention in the isomerization zone. Another advantage of the hydrogel route is a lower manufacturing cost due to reduced product yield loss and reduced number of heating steps. The catalysts prepared according to the invention have surface areas greater than about 275 $m^2/g$, and substantial portions, greater than about 40%, of their pore volume in pores having diameters less than about 50 Å.

DESCRIPTION OF THE PREFERRED EMBODIMENTS

This invention is a novel catalytic process to force movement of an alpha position double bond of an olefinic molecule to an interior position within said molecule by contacting the olefinic molecule, at isomerization conditions, with a catalyst prepared by incorporating palladium into an alumina hydrogel. This double bond isomerization process is a modification to an overall 3-step oligomerization, isomerization and disproportionation process used to produce a maximum quantity of $C_{12}$ to $C_{18}$ alpha olefins from an ethylene feed material.

Select linear alpha olefins, particularly in the carbon range of $C_{12}$ to $C_{18}$, can be produced from ethylene in an improved catalytic process having three essential integrated process steps: (1) oligomerization, (2) isomerization, and (3) disproportionation. The present invention is directed to an isomerization step which utilizes a catalyst prepared by incorporating palladium into an alumina hydrogel to diminish dimerization reactions during the olefin isomerization reaction while providing encouragement for the isomerization of the alpha olefin double bond to an internal position.

In the isomerization zone, high molecular weight alpha olefins and lower molecular weight alpha olefins are blended and balanced to a $C_{12}$ carbon atom range by the addition of $C_4$ olefins whereafter the alpha olefins are converted to internal olefins by double bond isomerization. The isomerization double bond migration procedure is carried out in a gas or liquid phase at isomerization conditions. Isomerization conditions typically include a temperature in the range of from about 0° C to about 500° C, a pressure in the range of from about 1.0 psig to about 2000 psig and a weight hourly space velocity in the range of from 0.1 to about 20. The preferred isomerization conditions include a temperature in the range of from about 100° C to about 150° C, a pressure in the range of from about 14 psig to about 2000 psig and a weight hourly space velocity in the range of from about 0.1 to about 20. The alpha olefins are isomerized in the presence of a catalyst prepared by incorporating palladium into an alumina hydrogel prepared by titrating an aqueous solution of an acid aluminum compound and an aqueous solution of a basic alumina compound, and subsequently calcining the hydrogel to prepare the catalyst.

The alumina hydrogel can be prepared by titrating an aqueous solution of one or more aluminum salt(s) with an appropriate acidic or basic material or solution to cause precipitation of the alumina gel. One skilled in the art will recognize that the alumina gel can be prepared by titrating an acidic aluminum salt such as, for example, aluminum sulfate, aluminum nitrate or aluminum chloride, in aqueous solution with a basic precipitating medium such as, for example, sodium hydroxide or ammonium hydroxide, or, by titrating an alkali metal aluminate such as, for example, sodium aluminate or potassium aluminate, in aqueous solution with an acidic precipitating medium such as, for example, hydrochloric acid or nitric acid. One skilled in the art will recognize that the adjustment of the pH of an aluminum-containing solution to between about 5.5 and about 10.0 will result in precipitation of the aluminum as aluminum hydroxide or hydrated aluminum oxide.

In a preferred embodiment, the alumina hydrogel is prepared by titrating an aqueous solution of an alkali metal aluminate and an aqueous solution of an acid aluminum salt to cause precipitation of the alumina gel. Suitable acidic aluminum salts include aluminum sulfate, aluminum nitrate and aluminum chloride. A preferred species is aluminum chloride. Suitable alkali metal aluminates are sodium aluminate and potassium aluminate. The precipitation can be carried out by adding an aqueous solution of the basic aluminum species to an aqueous solution of the acidic aluminum species or the procedure can be reversed by adding an aqueous solution of the acidic aluminum species to an aqueous solution of the basic aluminum species (referred to as "sequential precipitation"). Preferably, the precipitation in the instant invention is carried out by simultaneously adding the acid aluminum species and the basic aluminum species to cause precipitation of the hydrogel (referred to as "simultaneous precipitation"). The maximum rate of the addition of the acid aluminum species and the basic aluminum species is fixed by the rate at which the two streams can be mixed and the pH and the temperature of the system can be effectively controlled.

The ranges and limitations provided in the instant specification and claims are those which are believed to particularly point out and distinctly claim the instant invention. It is, however, understood that other ranges and limitations that perform substantially the same function in substantially the same manner to obtain the same result are intended to be within the scope of the instant invention as defined by the instant specification and claims.

The temperature and the pH of the precipitation are important variables in the preparation of the aluminas into which the palladium can be incorporated to form catalysts with desirable physical qualities. One skilled in the art would recognize that changes in precipitation temperatures and pHs result in changes in porosities. The optimal temperatures and pHs for the precipitation of the aluminas can be determined with a minimal amount of routine experimentation. In the instant invention, a precipitation temperature typically ranges from about 20° C to about 90° C, preferably from about 50° C to about 85° C, more preferably from about 55° C to about 65° C, and a precipitation pH typically ranges from about 5.5 to about 10.0, preferably between about 5.5 and about 8.0, and more preferably between about 6.0 and about 7.5. The length of time required for the precipitation step is typically from about 15 minutes to about 45 minutes. The period of time for the precipitation should be sufficiently long for adequate mixing of the materials, but not long enough for enhanced particle growth to occur.

After the precipitation step is completed, the pH of the slurry is adjusted by the addition of the basic aluminate solution to fall in the range from about 8.0 to about 12.0, preferably from about 9.0 to about 11.0, most preferably from about 9.5 to about 10.5, and aged at a temperature in the range from about 20° C to about 90° C, preferably from about 50° C to about 85° C for at least about 15 minutes. An upper limit on the length of time for aging is not critical and is normally determined by economical considerations. Aging times will typically range from about 0.1 to about 10 hours, preferably from about 0.25 to about 5 hours, and more preferably from about 0.25 to about 1 hour. In general, aluminas with acceptable properties are produced by holding the aging temperature equal to the precipitation temperature.

After aging, the slurry is washed and filtered in routine fashion to remove substantially all of the water-soluble salts formed during the precipitation of the hydrogel. The preferred solvent for washing is water although other solvents such as lower alkanols may be utilized.

After washing, the palladium is incorporated into the hydrogel. One method for adding the palladium to the hydrogel is a reslurry step in which the hydrogel is reslurried with a solution containing solubilized salts of palladium sufficient to deposit on the final catalyst from about 0.01 weight percent to about 10.0 weight percent palladium. The solution may, however, contain amounts of palladium in excess of that required to deposit the aforesaid amount of palladium, which excess may be removed by washing or other techniques following the reslurry step.

The palladium solution consists of a water-soluble source of palladium dissolved in water. Suitable palladium compounds include the palladium carboxylates, particularly palladium carboxylates derived from alkanoic acids containing up to 6 carbon atoms such as palladium acetate, complexes such as palladium acetylacetonate, bis-benzonitrile palladium (11) and lithium palladous chloride, as well as the palladium halides, nitrates and sulfates such as, for example, palladous chloride, palladium nitrate and palladium sulfate. The preferred palladium compound is tetraammine palladium(II) nitrate.

An alternative method for incorporating the palladium into the hydrogel is to add dry, water-soluble palladium salts to the hydrogel and mix until dissolution and adsorption of the palladium salts onto the gel is substantially complete. The palladium is added to the hydrogel in the amounts sufficient to incorporate into the final catalyst from about 0.01 weight percent to about 10.0 weight percent, preferably from about 0.1 weight percent to about 2.5 weight percent palladium. Palladium is generally added to the hydrogel in the form of dry, water-soluble salts of palladium chloride, palladium bromide, palladium iodide, palladium nitrate, palladium sulfate or palladium acetate, with tetraammine palladium (II) nitrate being preferred.

The dry salts of palladium are typically added to the hydrogel in the form of finely divided particles which are generally 100 mesh or less in size. While particle size is not critical and larger particle sizes may be utilized, it is economically advantageous to use particles which are 100 mesh or less in size.

The temperature and pH of the step in which the palladium solution and/or the dry palladium salts are mixed with the hydrogel are important variables in the preparation of hydrogel-derived catalysts which have acceptable densities and porosities. The mixing step is typically carried out at a pH in the range between about 4.0 and 10.0, preferably between about 4.0 and about 8.0, and a temperature in the range between about 25° C and about 100° C, preferably between about 25° C and about 80° C, until incorporation of the palladium salts into the gel is sufficient to yield a final calcined catalyst having from about 0.01 weight percent to about 10.0 weight percent palladium. Typically, the times for mixing the hydrogel and the palladium will range from about 0.5 to about 2 hours. Optionally, the resulting material can be washed to removed unadsorbed metals and filtered in routine fashion.

Following the addition of the palladium to the hydrogel, the resulting material is processed in one of many routine methods to produce the finished catalyst. The material may be extruded and then dried and calcined; dried, mulled with the addition of water and then extruded or pelleted and calcined; or partially dried, extruded or pelleted, dried more completely and calcined.

In a preferred embodiment, the resulting material is subjected to shearing in order to produce a stiffened hydrogel composition. The shearing of the hydrogel particles is accomplished by passing the hydrogel through a homogenizer such as, for example, a spring-loaded homogenization valve. The extent of shearing can be defined numerically by passing the hydrogel through a spring-loaded homogenization valve. A suitable degree of shear will normally be produced by a pressure drop in the range of from about 500 pounds per square inch to about 8000 pounds per square inch, preferably from about 2000 pounds per square inch to about 7000 pounds per square inch, on an ordinary spring-loaded homogenizer such as, for example, a Gaulin 15 gallons per hour, 8000 pounds per square inch Laboratory homogenizer. Shearing can also be affected by other means such as, for example, by use of a high-speed blender, but a homogenizer is preferred for continuous processing. The proper degree of shear in any event is that amount which produces an extrudate of the hydrogel which will not deform substantially under its own weight as formed. Thus, the extrudate formed prior to drying and calcining will retain its shape and enable the drying and calcining steps to be carried out without substantial change in shape.

After subjecting the hydrogel to shearing, the resulting material can then be readily extruded through an orifice ranging from about 0.05 to about 0.5 inches in diameter. It is generally preferable to extrude the discharge from the homogenizer directly through the orifice using the back pressure of the homogenizer as the driving force for extrusion. Where other means are used to effect shearing, suitable pumping means can be utilized to extrude the material through an extrusion header.

After extrusion, the extrudates are dried and calcined. Although it is possible to dry the extrudates in a single stage, it is preferred that the extrudate be dried in multiple stages. In multiple stages, a first drying step, called, "skin drying" is carried out to remove a substantial amount of the water and to form a dried skin on the surface of the extrudate. Skin drying is carried out at a temperature in the range of from about 100° C to about 300° C, preferably from about 120° C to about 200° C. These skin-dried extrudates may be handled and/or stored, if desired, without serious break-up of their structure before the final drying step. Final drying is accomplished by conventional means. It may be carried out by forced draft drying, vacuum drying, air drying or similar means. Drying temperatures are not critical and depend upon the particular means utilized for drying. Drying temperatures will typically range from about 50° C to about 200° C.

After drying, the material is calcined to produce the finished catalyst. The material may be calcined in an oxidizing or neutral atmosphere, although air is preferrred. However, if binders and/or lubricants are used, the material is heated in an oxygen-containing atmosphere, preferably air, in order to burn out the binders and lubricants. Calcining temperatures will typically range from about 300° C to about 900° C. Burn-out temperatures will depend on the concentration of oxygen in the burn-out atmosphere as well as the burn-out time involved. Typically, burn-out temperatures will range from about 300° C to about 900° C. Drying, calcining and burn-out may be combined in one or two steps. Most frequently, the calcining and/or burn-out steps are combined using an oxygen-containing atmosphere.

Certain other processing steps may be incorporated into the above-described procedure without deviating from the scope and intent of this invention.

The final catalysts are found to have surface areas greater than about 275 m²/g, nitrogen pore volumes ranging from about 0.30 to about 0.80 cc/g and at least about 40% of their mercury pore volume in pores having diameters less than about 50 Å. In general, the palladium content of the final catalyst ranges from about 0.01 weight percent to about 10.0 weight percent, preferably from about 0.1 weight percent to about 2.5 weight percent palladium.

The instant isomerization of the alpha olefin double bond is a non-skeletal isomerization, which may be exemplified by the izomerization of 1-hexadecene. During this isomerization, the double bond at the 1 position is moved to the 2 position, the 3 position, the 4 position, the 5 position, the 6 position, the 7 position and the 8 position. Where the isomer distribution is obtained at 80 to 100% of the calculated equilibrium isomer distribution, this equilibrium will comprise from about 10% to about 30% at the 2 position, about 10% to about 20% at the 3 position, about 10% to about 20% at the 4 position, about 10% to about 20% at the 5 position, about 5% to about 20% at the 6 position, about 5% to about 20% at the 7 position and about 2% to about 10% at the 8 position. A small residual amount (less than 2%) of the alpha olefin may also be present. These particular internal olefins are disproportionated to form the select $C_{11}$ to $C_{14}$ olefins, which can undergo hydroformylation to alcohols and aldehydes.

The oligomerization zone has ethylene or another even number lower olefin fed thereto to prepare long chain linear alpha olefins. This zone is conducted and maintained at oligomerization conditions comprising a temperature of from about 65° C to about 120° C and a pressure of from about 1000 psig to about 2000 psig. It is standard practice to employ an oligomerization catalyst to maximize the amount of linear alpha olefins produced. It is conceivable that the alpha olefins have a carbon range of from about 4 to as high as about 100. Suitable oligomerization catalysts include Ziegler-type catalysts such as lithium, sodium, potassium, beryllium and magnesium metal catalysts. Suitable Ziegler-type catalysts employed in ethylene oligomerization are described in U.S. Pat. Nos. 2,699,457, 3,310,600, 3,478,124 and 3,482,000, all of the teachings of which are incorporated by reference herein.

Another suitable class of ethylene oligomerization catalysts are nickel chelates of phosphorus containing bidentate ligands. Specific examples of these catalysts are nickel chelates of bidentate ligands having a tertiary organophosphorus moiety and a carboxymethyl or carboxyethyl group attached directly to the phosphorus atom of the organophosphorus moiety.

The effluent from the oligomerization zone contains olefins ranging from $C_4$ to $C_{100}$. The exact distribution is dependent upon the conditions in the oligomerization zone and the catalyst selected to promote the formation of the long chain olefins. It is desirable to maintain the oligomerization zone under conditions sufficient to maximize the quantity of $C_{12}$ to $C_{18}$ alpha olefins. The effluent from the oligomerization zone is passed to a first separation zone which is maintained at a temperature of about −10° C to about 300° C and a pressure of from about 0.4 psig to about 650 psig. The separation of the olefins is carried out in a separation zone in order to acquire a first alpha olefin product having from 12 to 18 carbon atoms. Two other streams are formed in the first separation zone, one being a light olefin stream having from $C_4$ to $C_{10}$ and the second being a heavy olefin stream having $C_{20}$ to $C_{100}$. This process seeks to recapture these lighter and heavier olefins from the separation zone and reprocess them to a desired carbon range of 11 to 14. These two streams are blended and will be converted in a purification-isomerization-disproportionation zone in order to modify them to the desired $C_{11}$ to $C_{14}$. For this reason, this combined effluent stream of light and heavy olefins is blended with a $C_4$ olefin in an amount calculated to average $C_{12}$.

This combined stream is passed to a purification zone wherein the stream is purged of isomerization and disproportionation catalyst poisons comprising oxygenates, metallic ions, water and inorganics. It is preferred that the various impurities are absorbed on an absorbant comprising a refractory inorganic oxide. Suitable refractory inorganic oxides include alumina, silica, zirconia, magnesia, silica-alumina, silica-alumina-chromium, and the like. The only requirement of this absorbent bed is that it be selective for the absorption of these poisonous compounds while permitting elution of the olefins to the isomerization zone. It is contemplated that these impurities may be drained from the purification zone and the absorbent may be regenerated in any convenient manner in order to renew or replace the refractory inorganic oxide absorbent.

The effluent derived from the purification zone, i.e. purified olefins having carbon ranges from $C_4$ to $C_{10}$ and $C_{20}$ to $C_{100}$ and balanced to $C_{12}$ are added to the isomerization zone above discussed wherein the hydrogel-derived palladium isomerization catalyst of this invention will modify the alpha olefins to interior olefins. An isomerization equilibrium is eventually arrived at with the double bond migrating between different positions in the olefin molecule. The isomerization, which is undertaken in the isomerization step, is one that is not considered skeletal. This type of movement of the double bond has heretofore not been recognized in the presence of a hydrogel-derived palladium catalyst.

The effluent passing from the isomerization step is a compilation of different internal olefins with almost no alpha olefins. These olefin molecules are rearranged in a disproportionation zone such that the higher molecular weight olefins are reacted with lower molecular weight olefins to yield olefins of intermediate molecular weight. The preferred length of the molecule is $C_{11}$ to $C_{14}$ By way of illustration, a higher olefin such as a 15-triacontene reacted with 2-butene is disproportionated into two molecules of 2-heptadecene. Similarly, 4-tetracosene is disproportionated in the presence of 2-butene into 2-hexene and 2-docosane.

The disproportionation step is performed under disproportionation conditions which include a reaction temperature in the range of from about 100° C to about 150° C and a pressure in the range of from about 150 psig to about 250 psig. The disproportionation is performed in the presence of a disproportionation catalyst which may be exemplified by cobalt and molybdenum metals deposited on an inorganic oxide support. These metals may be present in a weight percent of from about 1 wt % to about 15 wt % molybdenum and from about 0 wt % or 0.1 wt % to about 5 wt % cobalt. This catalyst can also be admixed with an alkali or alkaline earth metal to further the disproportionation. Other disproportionation catalysts will include Group VIB oxides such as rhenium supported on a refractory inorganic oxide such as alumina or silica. The disproportionation reaction is usually effected in a liquid phase in the presence of ethylene and if desired, liquid reaction diluents are utilized. Suitable diluents include hydrocarbons free from aliphatic unsaturation, such as acyclic or alicyclic alkenes of from 6 to 12 carbon atoms, i.e., hexane, isooctane and cyclohexane. Also exemplary are monoaromatic compounds such as benzene and toluene. If the diluent is added, it is present in amounts up to 20 moles of diluent per mole of olefinic reactants.

It should also be appreciated that the olefin products from the disproportionation zone will contain even and odd numbered carbon atoms whereas only even numbered olefins are produced in the ethylene oligomerization zone. It is also feasible to combine the isomerization and disproportionation steps into one unitary reaction containing the hydrogel-derived palladium catalyst of the isomerization zone and the preferred disproportionation catalyst of the disproportionation zone. In the event of simultaneous isomerization and disproportionation, the reaction conditions will depend in part upon the particular catalyst employed but generally will include a temperature of about 25° C to about 300° C and a pressure of from about 1 atmosphere to about 80 atmospheres. The olefins are contacted for a period of time ranging from about 30 minutes to about 1000 hours. The catalyst may be present in a pellet form with the isomerization and disproportionation catalyst being physically admixed and added to a unitary isomerization-disproportionation zone.

The reactor effluent from the disproportionation zone is passed to a second separation zone maintained at separation conditions of from about 30° C to about 350° C and a pressure of from about 1 psig to about 200 psig. A second higher olefin product stream is withdrawn from the second separation zone similar to the high olefin product stream derived from the first separation zone. These olefins may be mixed in tandem or sold individually as high olefin product streams. The second separation zone will function in a similar manner to the first separation zone in that a light olefin fraction having from $C_4$ to $C_{100}$ and a heavy olefin fraction having from $C_{15}$ to $C_{100}$ will be produced. It is possible that these streams can be further combined and processed in the same manner as the two non-product streams obtained from the first separation zone. In order to maximize the amount of $C_{11}$ to $C_{14}$ olefins, the latter recombination step can be undertaken or these olefins can be recycled to the process. In the event the heavy olefins having from $C_{15}$ to $C_{100}$ are recycled, it is preferred that they be combined with the heavy and light olefins derived from the first separation zone before admixture with the $C_4$ olefin to acquire the average carbon number of 12. If the recycle of the second separation stage light olefins is desired, this may be charged to the isomerization zone for further processing.

DETAILED DESCRIPTION OF THE DRAWING

Figure 1:
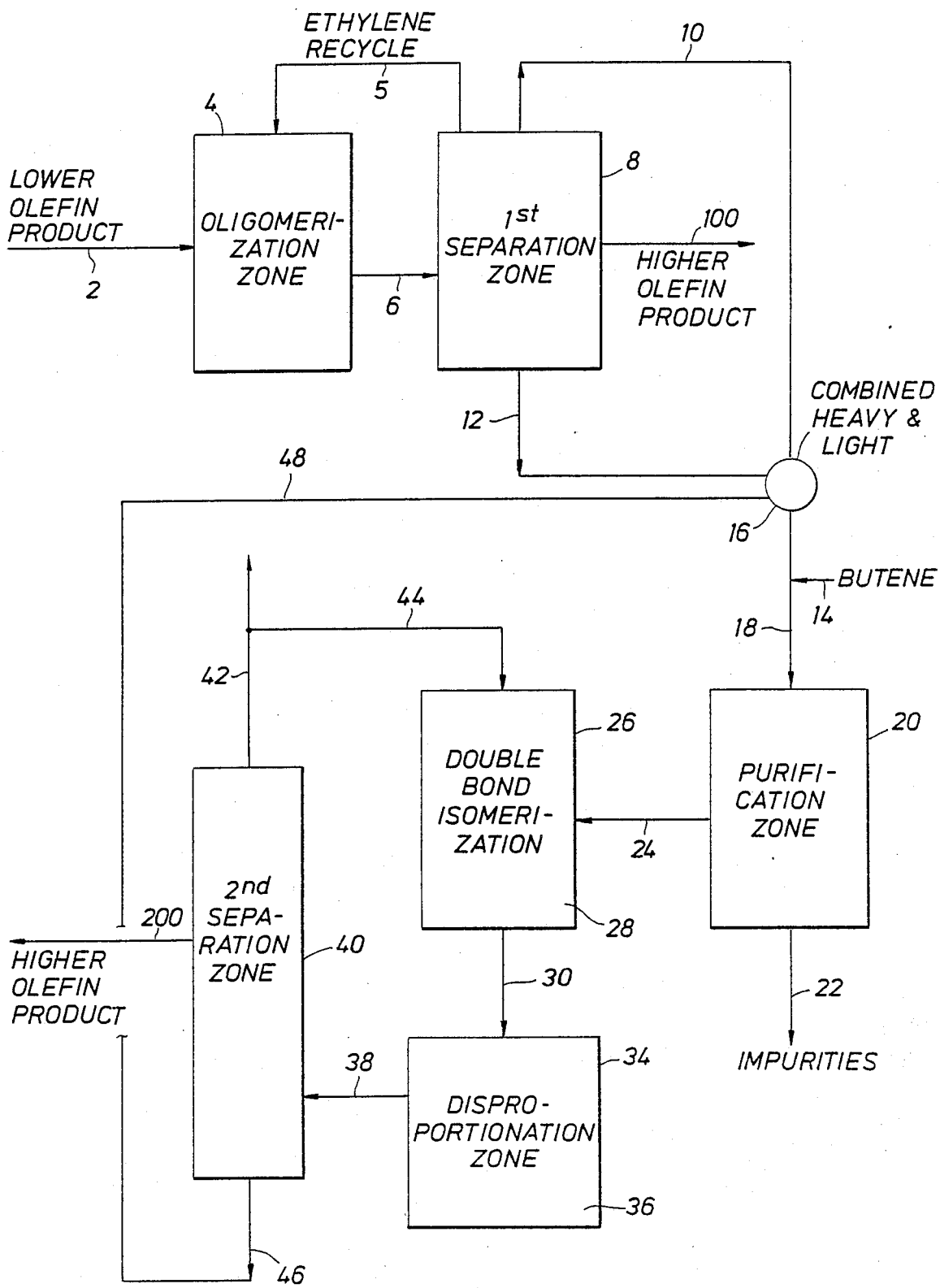
FIG. 1 is a schematic flow scheme of one embodiment of the process of this invention.

The instant flow scheme derives two higher olefin product streams from respective separation zones 8 and 40, i.e. higher olefin product stream 100 and higher olefin product stream 200. These streams are derived by a first charge to oligomerization zone 4 of a lower olefin, preferably ethylene, via conduit 2. The oligomerization zone is maintained in the presence of an oligomerization catalyst to maximize, where possible, the quantity of $C_{12}$ to $C_{18}$ olefins. The effluent from the oligomerization zone is passed through conduit 6 containing olefins from $C_2$ to $C_{100}$ which necessitate separation. This is accomplished in first separation zone 8 maintained under conditions sufficient to maximize separation of a $C_{12}$ to $C_{18}$ first olefin product stream in conduit 100. This product may be either further processed to alcohols or aldehydes, or if desired, sold as is. A light olefin top stream is derived from the first separation zone and comprises an ethylene recycle stream removed through conduit 5. Light alpha olefins having from $C_4$ up to $C_{10}$ are removed through conduit 10 and a bottoms stream is removed via conduit 12 containing olefins having from $C_{20}$ to $C_{100}$. If desired, all or a portion of the light olefin stream may be sold for its hydrocarbon qualities. The continued processing of at least one and preferably both of these two streams, 10 and 12, is critical to the success of the overall select olefin production of this process. These streams are combined with the addition of butene added by conduit 14 after their admixture in a zone or area generally referred to as 16 in the instant drawing. It is conceivable that a recycle stream may be provided from the second separation zone via 48 and thereafter butene is added to equate the average molecular weight of the olefin materials to approximately $C_{12}$. These olefins are passed along with certain undesirable impurities to a purification zone wherein an absorbent bed selective for absorption of the impurities is provided. This absorption bed can be an inorganic refractory oxide, such as alumina or another type of molecular sieve whereby oxygenates, metal ions, water, inorganics and other impurities are absorbed to provide cleansing of the overall olefin feed charged to purification zone 20 in conduit 18. Intermittently, impurities may be removed from the absorbent zone via removal conduit 22 and the absorption zone either be replaced or the absorbent bed regenerated by means not shown in the instant drawing. The effluent 24 from purification zone 20, is charged to double bond isomerization zone 26 containing the hydrogel-derived palladium catalyst generally shown as 28. With the hydrogel-derived palladium catalyst, the amount of dimerization which occurs during isomerization is reduced. The effluent from double bond isomerization zone 26 is withdrawn through conduit 30 and passed to disproportionation zone 34. In the disproportionation zone, two molecules of internal olefins disproportionate to produce higher and lower internal olefinic products. The olefins which are not considered alpha olefins, will be isomerized to the alpha position either during disproportionation or will be isomerized during subsequent hydroformylation in the presence of a hydroformylation catalyst. The disproportionation zone will also contain a disproportionation catalyst 36. The effluent from the disproportionation zone contains olefins having a carbon number of from 2 to 100. The disproportionation zone is maintained at conditions to maximize the quantity of $C_{12}$ to $C_{18}$ olefins. The disproportionation zone effluent 38 is passed to a second separation zone 40 maintained at conditions effective to separate a $C_{12}$ to $C_{18}$ higher olefin product in conduit 200. A light olefin material having a carbon number from $C_2$ to $C_{10}$ is withdrawn from the second separation zone 40 via conduit 42 and a portion of the same may be recycled to the double bond isomerization zone 26 by means of conduit 44. A heavy olefin material is withdrawn from the second separation zone 40 through conduit 46 and a portion of the same may be admixed with the combined light and heavy olefins separated from the first separation zone 8 in mixing area 16 by means of conduit 48.

The instant drawing has been provided as a schematic scheme to exemplify the process of this invention and should not be construed as a limitation thereupon.

The process of the instant invention will be further described below by the following examples which are illustrative and which are not to be construed as limiting the invention.

ILLUSTRATIVE EMBODIMENTS

Catalyst Preparation

Catalyst A 98.7 kilograms of aluminum sulfate solution were prepared by solubilizing 11.3 kilograms of gibbsite (alpha-alumina trihydrate, 34% LOI) in 87.4 kilograms of 27% sulfuric acid at a temperature slightly above 100° C. The solution was allowed to cool to 60° C prior to use. 76.2 kilograms of sodium aluminate solution were prepared by solubilizing 28.3 kilograms of gibbsite (alpha-alumina trihydrate, 34% LOI) in 47.9 kilograms 36% sodium hydroxide at a temperature slightly above 115° C. This solution was allowed to cool to 60° C prior to use. These two solutions were metered under computer control into a precipitation vessel containing a deionized water heel (140 kilograms) held at 60° C, maintaining a constant pH of 6.95 and a temperature of 60° C. The precipitation duration was fixed at 45 minutes. After the precipitation step was complete, excess sodium aluminate solution (8.7 kilograms) was added to the slurry to raise the pH to the desired aging pH of 10.2. Total solution quantities used: acid-43.2 kilograms, base-33.1 kilograms. The slurry was aged for one hour at the elevated pH. The slurry was then filtered in a single step on a 1' x 10' horizontal belt vacuum filter and washed with deionized water. The resulting alumina hydrogel generally had a water content between 75% and 90%, basis dry weight of alumina.

Into a vessel equipped with a high speed stirrer were added a portion of alumina hydrogel prepared above (4000 g, 84.78% LOI-608.8 g dry weight basis) and tetraammine palladium (II) nitrate (1.486 g). The mixture was stirred vigorously to "liquefy" the hydrogel. After reaction for 2 hours at 25° C, the catalyst hydrogel slurry was passed through a Gaulin Model 15M Lab Homogenizer using a pressure drop of 6000 psi. The stiffened material from this homogenization step was extruded using a small, hand-extruder. Drying of the extrudate at 150° C was followed by calcination at 450° C for two hours. The properties of the catalyst are listed in Table I.

Catalyst B 98.7 kilograms of aluminum sulfate solution were prepared by solubilizing 11.3 kilograms of gibbsite (alpha-alumina trihydrate, 34% LOI) in 87.4 kilograms of 27% sulfuric acid at a temperature slightly above 100° C. The solution was allowed to cool to 60° C prior to use. 76.2 kilograms of sodium aluminate solution were prepared by solubilizing 28.3 kilograms of gibbsite (alpha-alumina trihydrate, 34% LOI) in 47.9 kilograms 36% sodium hydroxide at a temperature slightly above 115° C. This solution was allowed to cool to 60° C prior to use. These two solutions were metered under computer control into a precipitation vessel containing a deionized water heel (40 kilograms) held at 60° C, maintaining a constant pH of 6.95 and a temperature of 60° C. The precipitation duration was fixed at 45 minutes. After the precipitation step was complete, excess sodium aluminate solution (8.7 kilograms) was added to the slurry to raise the pH to the desired aging pH of 10.2. Total solution quantities used: acid-43.2 kilograms, base-33.1 kilograms. The slurry was aged for one hour at the elevated pH. The slurry was then filtered in a single step on a 1' x 10' horizontal belt vacuum filter and washed with deionized water. The resulting alumina hydrogel generally had a water content between 75% and 90%, basis dry weight of alumina.

Into a vessel equipped with a high speed stirrer were added a portion of alumina hydrogel prepared above (4000 g, 84.78% LOI-608.8 g dry weight basis) and tetraammine palladium (II) nitrate (15.0 g). The mixture was stirred vigorously to "liquefy" the hydrogel. After reaction for 2 hours at 25° C, the catalyst hydrogel slurry was passed through a Gaulin Model 15M Lab Homogenizer using a pressure drop of 6000 psi. The stiffened material from this homogenization step was extruded using a small, hand-extruder. Drying of the extrudate at 150° C was followed by calcination at 450° C for two hours. The properties of the catalyst are listed in Table I.

Catalyst C

Catalyst C was prepared using a conventional dry pore volume impregnation technique. A solution suitable for impregnating 15.5 grams of calcined alumina support with a pore volume of 0.75 cc/g was prepared as follows. An impregnation solution was made by combining 0.443 g of an aqueous tetraammine palladium (II) nitrate solution containing 0.035 g Pd/g solution and enough deionized water such that the solution had a total volume of 12 milliliters. After adding the entire solution to the alumina support in several small portions with intermediate agitations, the impregnated support was dried overnight at 150° C and calcined in air for two hours at 450° C. The properties of the catalyst are listed in the Table I.

Catalyst D

Catalyst D was prepared using a conventional dry pore volume impregnation technique. A solution suitable for impregnating 15.5 grams of calcined alumina support with a pore volume of 0.75 cc/g was prepared as follows. An impregnation solution was made by combining 4.43 g of an aqueous tetraammine palladium (II) nitrate solution containing 0.035 g Pd/g solution and enough deionized water such that the solution had a total volume of 12 milliliters. After adding the entire solution to the alumina support in several small portions with intermediate agitations, the impregnated support was dried overnight at 150° C and calcined in air for two hours at 450° C. The properties of the catalyst are listed in the Table I.

Catalyst Testing 20 cm$^3$ of undiluted 1/32" catalyst extrudates were charged to a cylindrical 0.60" ID stainless steel reactor equipped with an 0.19" internal thermowell. This gave an overall catalyst bed length of approximately 8". A catalyst was activated by treatment with flowing H$_2$ at 1 atmosphere of pressure and 650° F for 1.5 hours. Following reduction, the catalyst was cooled under N$_2$ to 250° F and prepurified 1-hexadecene introduced as feed. After start up, reactor temperatures were adjusted to attain equilibrium conversion of feed. At the completion of a test run, each catalyst was N$_2$ stripped at 400° F. Products were analyzed using standard gas chromatographic methods. The results of catalyst testing are found in Tables II-IX.

From the data presented in these Tables, it is evident that the hydrogel-derived catalysts, Catalysts A and B, are as active for olefin double bond isomerization as the conventionally prepared catalysts, Catalysts C and D, but they produce no dimeric reaction side products. Dimeric reaction side products result in the loss of valuable reaction product and are thus undesirable. The fact that no dimeric products are obtained using Catalysts A and B gives these catalysts a selectivity advantage over the conventionally prepared catalysts, Catalysts C and D.

TABLE I

| | Catalyst Properties | | | |
|---|---|---|---|---|
| Catalyst | A | B | C | D |
| Wt. % Palladium[a] | 0.1 | 1.0 | 0.1 | 1.0 |
| Surface Area[b] m$^2$/gm | 376 | 308 | 253 | 243 |
| Pore Volume[c] cc/gm | 0.47 | 0.42 | 0.67 | 0.64 |
| Compacted Bulk Density[d] gm/cc | 0.80 | 0.83 | 0.62 | 0.62 |
| Hg Pore Size Distribution[e] | | | | |
| <50Å | 88.2 | 88.0 | 6.4 | 7.9 |
| 50-70Å | 4.2 | 5.2 | 28.8 | 26.9 |
| 70-100Å | 2.5 | 2.2 | 47.2 | 46.8 |
| 100-150Å | 2.1 | 2.1 | 8.4 | 9.4 |
| 150-350Å | 2.1 | 2.0 | 4.9 | 5.0 |
| >350Å | 0.8 | 0.4 | 4.4 | 4.0 |
| Average Pore Size | 44.8 | 46.3 | 76.5 | 76.1 |

[a]Weight percent determined by neutron activation analysis or atomic absorption spectroscopy.
[b]BET, by nitrogen adsorption/desorption, Micromeritics Digisorb 2500 Instrument.
[c]By nitrogen adsorption, Micromeritics Digisorb 2500 Instrument.
[d]209 cc volume fully settled in a graduated cup and weighed.
[e]Determined by mercury intrusion, to 60,000 psi using a Micromeritics Autopore 9210, using a 130° contact angle and 0.473 N/m surface tension of mercury. Numbers listed are percent pore volume except the average pore size which is listed in angstroms.

TABLE II

Olefin Double Bond Isomerization Activity of Catayst A Using 1-Hexadecene Olefin Feed

| Exp. No. | Tem. °F. | Cat. Hrs. | WHSV | % C$_{16}$ DB Iso | % Dimer | % C$_{16}$ Branch. | Net C$_{16}$ Branch. | % Dimer/% Branch. |
|---|---|---|---|---|---|---|---|---|
| 1 | 252 | 17 | 1.7 | 69.0 | 0.00 | 2.50 | 0.01 | 0.00 |
| 2 | 292 | 41 | 1.7 | 88.0 | 0.00 | 2.51 | 0.02 | 0.00 |
| 3 | 292 | 64 | 1.7 | 89.0 | 0.00 | 2.51 | 0.02 | 0.00 |
| 4 | 327 | 136 | 1.7 | 97.0 | 0.00 | 2.51 | 0.02 | 0.00 |
| 5 | 327 | 160 | 1.7 | 98.0 | 0.00 | 2.51 | 0.02 | 0.00 |
| 6 | 327 | 184 | 1.7 | 98.0 | 0.00 | 2.51 | 0.02 | 0.00 |
| 7 | 327 | 208 | 1.7 | 98.0 | 0.00 | 2.51 | 0.02 | 0.00 |
| 8 | 327 | 232 | 1.7 | 98.0 | 0.00 | 2.57 | 0.08 | 0.00 |

TABLE III

Olefin Double Bond Distribution of Isomerized C$_{16}$ Over Catalyst A Using 1-Hexadecene Feed

| Test No. | % C$_{16}$ DB Iso. | 1-C$_{16}$ | 2-C$_{16}$ | 3-C$_{16}$ | 4-C$_{16}$ | 5-C$_{16}$ | 6-C$_{16}$ | 7-C$_{16}$ | 8-C$_{16}$ | Beta/Alpha |
|---|---|---|---|---|---|---|---|---|---|---|
| 1 | 69.0 | 4.4 | 31.1 | 20.7 | 14.8 | 12.3 | 7.3 | 6.2 | 3.2 | 7.1 |
| 2 | 88.0 | 2.0 | 20.5 | 16.7 | 16.8 | 15.2 | 12.2 | 11.1 | 5.5 | 10.3 |
| 3 | 89.0 | 1.8 | 20.2 | 16.6 | 16.9 | 15.3 | 12.4 | 11.3 | 5.6 | 11.2 |
| 4 | 97.0 | 1.6 | 16.0 | 14.0 | 16.9 | 15.3 | 15.0 | 14.2 | 6.9 | 10.0 |
| 5 | 98.0 | 1.6 | 15.5 | 13.8 | 16.9 | 15.3 | 15.3 | 14.6 | 7.0 | 9.7 |
| 6 | 98.0 | 1.6 | 15.3 | 13.5 | 16.9 | 15.3 | 15.5 | 14.7 | 7.1 | 9.6 |
| 7 | 98.0 | 1.5 | 15.1 | 13.6 | 16.9 | 15.3 | 15.6 | 14.8 | 7.1 | 10.1 |
| 8 | 98.0 | 1.6 | 15.1 | 13.6 | 16.9 | 15.3 | 15.5 | 14.8 | 7.1 | 9.4 |

TABLE IV

Olefin Double Bond Isomerization Activity of Catalyst B Using 1-Hexadecene Olefin Feed

| Exp. No. | Tem. °F. | Cat. Hrs. | WHSV | % $C_{16}$ DB Iso. | % Dimer | % $C_{16}$ Branch. | Net $C_{16}$ Branch. | % Dimer/ % Branch. |
|---|---|---|---|---|---|---|---|---|
| 1 | 252 | 17 | 1.6 | 83.0 | 0.00 | 2.56 | 0.07 | 0.00 |
| 2 | 251 | 41 | 1.6 | 83.0 | 0.00 | 2.56 | 0.07 | 0.00 |
| 3 | 292 | 65 | 1.6 | 95.4 | 0.00 | 2.54 | 0.05 | 0.00 |
| 4 | 292 | 137 | 1.6 | 96.0 | 0.00 | 2.51 | 0.02 | 0.00 |
| 5 | 327 | 161 | 1.6 | 99.0 | 0.00 | 2.53 | 0.04 | 0.00 |
| 6 | 327 | 185 | 1.6 | 100.0 | 0.00 | 2.55 | 0.06 | 0.00 |
| 7 | 327 | 209 | 1.6 | 100.8 | 0.00 | 2.55 | 0.06 | 0.00 |
| 8 | 327 | 233 | 1.6 | 100.0 | 0.00 | 2.50 | 0.01 | 0.00 |

TABLE V

Olefin Double Bond Distributon of Isomerized $C_{16}$ Over Catalyst B Using 1-Hexadecene Feed

| Test No. | % $C_{16}$ DB Iso. | 1-$C_{16}$ | 2-$C_{16}$ | 3-$C_{16}$ | 4-$C_{16}$ | 5-$C_{16}$ | 6-$C_{16}$ | 7-$C_{16}$ | 8-$C_{16}$ | Beta/ Alpha |
|---|---|---|---|---|---|---|---|---|---|---|
| 1 | 83.0 | 3.2 | 24.1 | 16.6 | 15.8 | 13.7 | 11.3 | 10.2 | 5.0 | 7.5 |
| 2 | 83.0 | 1.8 | 24.9 | 17.0 | 16.0 | 13.9 | 11.3 | 10.1 | 5.0 | 13.8 |
| 3 | 95.4 | 1.6 | 17.6 | 14.2 | 16.7 | 15.0 | 14.6 | 13.7 | 6.6 | 11.0 |
| 4 | 96.0 | 1.4 | 16.7 | 14.0 | 16.9 | 15.2 | 14.9 | 14.0 | 6.8 | 11.9 |
| 5 | 99.0 | 1.5 | 14.9 | 13.1 | 16.8 | 15.2 | 15.9 | 15.3 | 7.3 | 9.9 |
| 6 | 100.0 | 1.4 | 14.4 | 13.0 | 16.9 | 15.2 | 16.2 | 15.5 | 7.4 | 10.3 |
| 7 | 100.8 | 1.4 | 14.4 | 12.9 | 16.8 | 15.2 | 16.2 | 15.6 | 7.4 | 10.3 |
| 8 | 100.0 | 1.5 | 14.4 | 12.9 | 16.8 | 15.1 | 16.2 | 15.6 | 7.5 | 9.6 |

TABLE VI

Olefin Double Bond Isomerization Activity of Catalyst C Using 1-Hexadecene Olefin Feed

| Exp. No. | Tem. °F. | Cat. Hrs. | WHSV | % $C_{16}$ DB Iso. | % Dimer | % $C_{16}$ Branch. | Net $C_{16}$ Branch. | % Dimer/ % Branch. |
|---|---|---|---|---|---|---|---|---|
| 1 | 253 | 19 | 2.1 | 79.0 | 0.00 | 2.49 | 0.00 | 0.00 |
| 2 | 291 | 91 | 2.1 | 95.9 | 0.00 | 2.48 | −0.01 | 0.00 |
| 3 | 291 | 115 | 2.2 | 96.9 | 0.00 | 2.51 | 0.02 | 0.00 |
| 4 | 291 | 139 | 2.1 | 97.0 | 0.01 | 2.47 | −0.02 | 0.00 |
| 5 | 291 | 163 | 2.1 | 97.0 | 0.01 | 2.48 | −0.01 | 0.00 |
| 6 | 291 | 187 | 2.1 | 97.0 | 0.00 | 2.46 | −0.03 | 0.00 |
| 7 | 291 | 259 | 2.0 | 97.0 | 0.01 | 2.50 | 0.01 | 0.00 |
| 8 | 291 | 283 | 2.0 | 97.0 | 0.00 | 2.51 | 0.02 | 0.00 |
| 9 | 291 | 307 | 2.1 | 97.0 | 0.00 | 2.50 | 0.01 | 0.00 |
| 10 | 291 | 331 | 2.0 | 97.0 | 0.01 | 2.42 | −0.07 | 0.00 |
| 11 | 291 | 355 | 2.1 | 97.0 | 0.01 | 2.45 | −0.04 | 0.00 |
| 12 | 299 | 428 | 2.0 | 98.0 | 0.01 | 2.67 | 0.18 | 0.00 |
| 13 | 299 | 452 | 2.0 | 98.0 | 0.01 | 2.48 | −0.01 | 0.00 |
| 14 | 326 | 476 | 2.0 | 100.7 | 0.01 | 2.54 | 0.05 | 0.00 |
| 15 | 326 | 500 | 2.1 | 101.3 | 0.02 | 2.41 | −0.08 | 0.01 |
| 16 | 326 | 524 | 2.1 | 101.0 | 0.02 | 2.54 | 0.05 | 0.01 |

TABLE VII

Olefin Double Bond Distribution of Isomerized $C_{16}$ Over Catalyst C Using 1-Hexadecene Feed

| Test No. | % $C_{16}$ DB Iso. | 1-$C_{16}$ | 2-$C_{16}$ | 3-$C_{16}$ | 4-$C_{16}$ | 5-$C_{16}$ | 6-$C_{16}$ | 7-$C_{16}$ | 8-$C_{16}$ | Beta/ Alpha |
|---|---|---|---|---|---|---|---|---|---|---|
| 1 | 79.0 | 2.4 | 25.2 | 19.0 | 16.6 | 14.8 | 9.5 | 8.3 | 4.2 | 10.5 |
| 2 | 95.9 | 1.3 | 16.8 | 14.2 | 17.4 | 16.1 | 14.4 | 13.4 | 6.5 | 12.9 |
| 3 | 96.9 | 1.2 | 16.2 | 14.0 | 17.4 | 16.0 | 14.7 | 13.8 | 6.7 | 13.5 |
| 4 | 97.0 | 1.3 | 16.2 | 14.0 | 17.0 | 15.5 | 15.0 | 14.1 | 6.8 | 12.5 |
| 5 | 97.0 | 1.5 | 16.1 | 14.0 | 17.0 | 15.5 | 15.0 | 14.1 | 6.8 | 10.7 |
| 6 | 97.0 | 1.4 | 16.1 | 14.1 | 17.0 | 15.5 | 15.0 | 14.1 | 6.8 | 11.5 |
| 7 | 97.0 | 1.4 | 16.1 | 14.0 | 17.0 | 15.5 | 15.0 | 14.1 | 6.8 | 11.5 |
| 8 | 97.0 | 1.4 | 16.1 | 14.0 | 17.0 | 15.5 | 15.0 | 14.1 | 6.8 | 11.5 |
| 9 | 97.0 | 1.4 | 16.2 | 14.0 | 17.0 | 15.5 | 15.0 | 14.1 | 6.8 | 11.6 |
| 10 | 97.0 | 1.4 | 16.0 | 14.1 | 17.1 | 15.5 | 15.0 | 14.1 | 6.8 | 11.4 |
| 11 | 97.0 | 1.4 | 16.4 | 14.0 | 17.0 | 15.5 | 14.9 | 14.0 | 6.8 | 11.7 |
| 12 | 98.0 | 1.4 | 15.4 | 13.6 | 17.0 | 15.5 | 15.4 | 14.7 | 7.1 | 11.0 |
| 13 | 98.0 | 1.4 | 15.3 | 13.5 | 17.0 | 15.4 | 15.5 | 14.8 | 7.1 | 10.9 |
| 14 | 100.7 | 1.6 | 14.4 | 12.8 | 16.8 | 15.2 | 16.2 | 15.5 | 7.4 | 9.0 |
| 15 | 101.3 | 1.6 | 14.1 | 12.7 | 16.8 | 15.2 | 16.3 | 15.7 | 7.5 | 8.8 |
| 16 | 101.0 | 1.4 | 14.0 | 12.7 | 16.8 | 15.2 | 16.5 | 15.9 | 7.6 | 10.0 |

TABLE VIII

Olefin Double Bond Isomerization Activity of Catalyst D Using 1-Hexadecene Olefin Feed

| Exp. No. | Tem. °F. | Cat. Hrs. | WHSV | % $C_{16}$ DB Iso. | % Dimer | % $C_{16}$ Branch. | Net $C_{16}$ Branch. | % Dimer/ % Branch. |
|---|---|---|---|---|---|---|---|---|
| 1 | 254 | 17 | 2.0 | 67.0 | 0.00 | 2.50 | 0.01 | 0.00 |
| 2 | 254 | 41 | 1.9 | 69.6 | 0.01 | 2.48 | −0.01 | 0.00 |
| 3 | 254 | 65 | 2.0 | 70.0 | 0.01 | 2.49 | 0.00 | 0.00 |
| 4 | 295 | 137 | 2.4 | 85.9 | 0.01 | 2.50 | 0.01 | 0.00 |
| 5 | 295 | 161 | 2.4 | 87.4 | 0.01 | 2.47 | −0.02 | 0.00 |
| 6 | 295 | 185 | 2.0 | 91.0 | 0.01 | 2.52 | 0.03 | 0.00 |
| 7 | 295 | 209 | 2.0 | 90.8 | 0.02 | 2.51 | 0.02 | 0.01 |
| 8 | 294 | 233 | 2.0 | 91.0 | 0.00 | 2.48 | −0.01 | 0.00 |
| 9 | 295 | 305 | 2.0 | 91.0 | 0.00 | 2.51 | 0.02 | 0.00 |
| 10 | 294 | 329 | 2.0 | 91.0 | 0.00 | 2.52 | 0.03 | 0.00 |
| 11 | 295 | 353 | 2.0 | 91.0 | 0.00 | 2.50 | 0.01 | 0.00 |
| 12 | 295 | 377 | 2.0 | 91.0 | 0.01 | 2.52 | 0.03 | 0.00 |
| 13 | 295 | 401 | 2.0 | 91.4 | 0.01 | 2.51 | 0.02 | 0.00 |
| 14 | 313 | 474 | 2.0 | 95.0 | 0.00 | 2.51 | 0.02 | 0.00 |
| 15 | 313 | 498 | 2.0 | 95.0 | 0.01 | 2.47 | −0.02 | 0.00 |
| 16 | 341 | 522 | 2.0 | 98.8 | 0.02 | 2.51 | 0.02 | 0.01 |
| 17 | 341 | 546 | 2.0 | 99.2 | 0.01 | 2.51 | 0.02 | 0.01 |
| 18 | 341 | 570 | 2.0 | 99.0 | 0.02 | 2.51 | 0.02 | 0.01 |

TABLE IX

Olefin Double Bond Distribution Isomerized $C_{16}$ Over Catalyst D Using 1-Hexadecene Feed

| Test No. | % $C_{16}$ DB Iso. | 1-$C_{16}$ | 2-$C_{16}$ | 3-$C_{16}$ | 4-$C_{16}$ | 5-$C_{16}$ | 6-$C_{16}$ | 7-$C_{16}$ | 8-$C_{16}$ | Beta/ Alpha |
|---|---|---|---|---|---|---|---|---|---|---|
| 1 | 67.0 | 4.2 | 35.4 | 19.2 | 13.8 | 11.0 | 7.2 | 6.1 | 3.1 | 8.4 |
| 2 | 69.6 | 2.7 | 35.1 | 19.5 | 14.2 | 11.5 | 7.5 | 6.4 | 3.3 | 13.0 |
| 3 | 70.0 | 2.5 | 34.6 | 19.4 | 14.3 | 11.7 | 7.7 | 6.6 | 3.3 | 13.8 |
| 4 | 85.9 | 1.8 | 23.5 | 16.6 | 16.2 | 14.2 | 11.8 | 10.7 | 5.3 | 13.1 |
| 5 | 87.4 | 1.8 | 22.4 | 16.1 | 16.4 | 14.6 | 12.2 | 11.1 | 5.5 | 12.4 |
| 6 | 91.0 | 1.7 | 20.2 | 15.5 | 16.4 | 14.6 | 13.3 | 12.3 | 6.0 | 11.9 |
| 7 | 90.8 | 1.5 | 20.3 | 15.5 | 16.7 | 15.0 | 13.1 | 12.0 | 5.9 | 13.5 |
| 8 | 91.0 | 1.7 | 20.1 | 15.5 | 16.4 | 14.6 | 13.4 | 12.3 | 6.0 | 11.8 |
| 9 | 91.0 | 1.8 | 20.1 | 15.4 | 16.4 | 14.5 | 13.4 | 12.3 | 6.0 | 11.2 |
| 10 | 91.0 | 1.7 | 19.8 | 15.3 | 16.5 | 14.6 | 13.5 | 12.5 | 6.1 | 11.6 |
| 11 | 91.0 | 1.7 | 19.8 | 15.4 | 16.5 | 14.6 | 13.5 | 12.5 | 6.1 | 11.6 |
| 12 | 91.0 | 1.7 | 19.8 | 15.4 | 16.5 | 14.6 | 13.5 | 12.4 | 6.1 | 11.6 |
| 13 | 91.4 | 1.7 | 19.9 | 15.4 | 16.4 | 14.6 | 13.5 | 12.4 | 6.1 | 11.7 |
| 14 | 95.0 | 1.6 | 17.5 | 14.4 | 16.6 | 14.9 | 14.6 | 13.7 | 6.6 | 10.9 |
| 15 | 95.0 | 1.6 | 17.2 | 14.2 | 16.6 | 14.9 | 14.8 | 13.9 | 6.7 | 10.7 |
| 16 | 98.8 | 1.7 | 15.5 | 13.3 | 16.7 | 15.0 | 15.7 | 14.9 | 7.2 | 9.1 |
| 17 | 99.2 | 1.6 | 15.3 | 13.4 | 16.7 | 15.0 | 15.8 | 15.1 | 7.2 | 9.6 |
| 18 | 99.0 | 1.6 | 15.1 | 13.3 | 16.7 | 15.0 | 15.8 | 15.1 | 7.3 | 9.4 |

I claim as my invention:

1. A double bond isomerization process for the conversion of an alpha olefin feedstock to a mixture of internal olefins, which process comprises contacting said olefin having an alpha double bond therein at isomerization conditions with a catalyst having a surface area of at least about 275 m²/g and at least about 40% of its pore volume in pores having diameters less than about 50 Å prepared by incorporating palladium into an alumina hydrogel.

2. The process of claim 1 wherein said isomerization conditions include a temperature of about 0° C to about 500° C, a pressure of from about 1.0 psig to about 2000 psig and a weight hourly space velocity of from about 0.1 to about 20.

3. The process of claim 1 wherein said alpha olefin feedstock has from $C_4$ to $C_{100}$ carbon atoms.

4. The process of claim 3 wherein said alpha olefin feedstock comprises a blend of olefins having $C_4$, $C_6$ to $C_{10}$ and $C_{15}$ to $C_{60}$ carbon atoms with the addition of $C_4$ olefins to balance the average carbon number distribution to about $C_{12}$.

5. The process of claim 1 wherein the distribution of internal olefins prepared from $C_{16}$ alpha olefin isomerization is at equilibrium equal to about 10% to about 30% at the 2 position about 10% to about 20% at the 3 position, about 10% to about 20% at the 4 position, about 10% to about 20% at the 5 position, about 5% to about 20% at the 6 position, about 5% to about 20% at the 7 position and about 2% to about 10% at the 8 position, wherein said isomer distribution is obtained at 80% to 100% of a calculated isomer distribution.

6. The process of claim 1 wherein said catalyst contains from about 0.01 weight percent to about 10.0 weight percent palladium.

7. The process of claim 6 wherein said catalyst contains from about 0.1 weight percent to about 2.5 weight percent palladium.

8. The process of claim 1 wherein said palladium is derived from tetraammine palladium (II) nitrate.

9. The process of claim 1 wherein said catalyst is prepared by a process which comprises:
   (a) titrating an aqueous solution of one or more aluminum salts(s) with a titrating agent, thereby forming a precipitate, (b) aging the precipitate at a temperature ranging from about 20° C to about 90° C for at least about 15 minutes at a pH ranging from about 8.0 to about 12.0, (c) washing the precipitate, (d) mixing the precipitate with palladium at a pH in the range between about 4.0 and about 10.0 and a temperature in the range between about 25° C and about 100° C until adsorption of the palladium onto the precipitate is sufficient to yield a final catalyst having from about 0.01 weight percent to about 10.0 weight percent palladium, (e) extruding the product of step (d), and (f) drying and calcining the product of step (e) at a temperature ranging from about 300° C to about 900° C.

10. A process for the increased production of higher olefins having alpha double bonds from ethylene which comprises:

(a) oligomerization of a feed material predominantly comprising ethylene in an ethylene oligomerization zone, at oligomerization conditions, in the presence of an oligomerization catalyst to form higher olefinic molecules having even carbon number of $C_4$ to $C_{100}$;

(b) separating said produced even numbered olefins in a first separation zone, at first separation zone conditions, to form a first olefin product stream having alpha double bonds and having from $C_{12}$ to $C_{18}$ and first separation zone effluent streams having: (1) unreacted ethylene, (2) light alpha olefins from $C_4$ to $C_{10}$ and (3) heavy alpha olefins having from $C_{20}$ to $C_{100}$;

(c) combining said light and heavy alpha olefins and passing said combined stream to purification-isomerization-disproportionation steps and balancing therewith a quantity of $C_4$ olefins to average the carbon number in said combined stream to approximately $C_{12}$;

(d) purifying said combined alpha olefin stream in the presence of a purification absorbent bed, at purification conditions, to remove from said combined stream impurities comprising oxygenates, metals, water and inorganics;

(e) double bond isomerizing, in an isomerization step, said purified alpha olefins of step (d), at isomerization conditions, in the presence of a hydrogel-derived palladium catalyst having a surface area of at least about 275 m²/g and at least about 40% of its pore volume in pores having diameters less than about 50 Å to thereby diminish the amount of dimerization during isomerization, wherein said isomerization produces an isomerization effluent stream having internal double bonds and being substantially free of alpha-situated double bonds;

(f) disproportionating said isomerization olefin stream produced in step (e) in a disproportionation step in the presence of a disproportionation catalyst maintained at disproportionation conditions, to form an effluent stream containing $C_{12}$–$C_{18}$ olefins and olefins lighter and heavier than $C_{12}$ and $C_{18}$; and (g) separating said disproportionation effluent stream of step (f) in a second separation zone maintained at second separation conditions to form a second olefin product stream having from $C_{10}$–$C_{18}$ carbon atoms and a light and heavy olefin fraction.

11. The process of claim 10 wherein said oligomerization catalyst comprises an organometallic compound and wherein said oligomerization conditions comprise a temperature of about 0° C to about 250° C and a pressure of from about 14 psig to about 3000 psig.

12. The process of claim 11 said oligomerization catalyst comprises an aluminum trialkyl wherein ethylene is oligomerized in the presence of said catalyst at a temperature of about 25° C and a pressure of about 550 psig.

13. The process of claim 11 wherein said oligomerization catalyst is prepared by contacting bis-1,5-cyclooctadiene nickel and diphenylcarboxymethylphosphine.

14. The process of claim 10 wherein said first separation zone is maintained at a temperature in the range of from about −10° C to about 300° C and a pressure in the range of from about 0.4 psig to about 650 psig to form said first olefin product stream having alpha double bonds and said first separation zone effluent streams having light alpha olefins of from $C_4$ to $C_{10}$ and heavy alpha olefins having from $C_{20}$ to $C_{100}$ carbon atoms.

15. The process of claim 10 wherein said purification absorbent bed comprises a refractory inorganic oxide.

16. The process of claim 15 wherein said refractory inorganic oxide is selected from the group consisting of alumina, silica, zirconia, magnesia, silica-alumina and silica-alumina-chromia.

17. The process of claim 10 wherein said purification conditions include a temperature in the range of from about 100° C to about 200° C and a pressure in the range of from about 1 psig to about 200 psig.

18. The process of claim 15 wherein said refractory inorganic oxide is selected for absorption of impurities comprising oxygenates, metallic ions, water and inorganics.

19. The process of claim 10 wherein said hydrogel-derived palladium catalyst in step (e) is prepared by incorporating palladium into an alumina hydrogel.

20. The process of claim 10 wherein said hydrogel-derived palladium catalyst in step (e) contains from about 0.01 weight percent palladium to about 10.0 weight percent palladium.

21. The process of claim 20 wherein said hydrogel-derived palladium catalyst in step (e) contains from about 0.1 weight percent to about 2.5 weight percent palladium.

22. The process of claim 10 wherein said palladium in said hydrogel-derived palladium catalyst in step (e) is derived from tetraammine palladium (II) nitrate.

23. The process of claim 10 wherein said hydrogel-derived palladium catalyst is prepared by a process which comprises:

(a) titrating an aqueous solution of one or more aluminum salts(s) with a titrating agent, thereby forming a precipitate, (b) aging the precipitate at a temperature ranging from about 20° C to about 90° C for at least about 15 minutes at a pH ranging from about 8.0 to about 12.0, (c) washing the precipitate, (d) mixing the precipitate with palladium at a pH in the range between about 4.0 and about 10.0 and a temperature in the range between about 25° C and about 100° C until adsorption of the palladium onto the precipitate is sufficient to yield a final catalyst having from about 0.01 weight percent to about 10.0 weight percent palladium, (e) extruding the product of step (d), and (f) drying and calcining the product of step (e) at a temperature ranging from about 300° C to about 900° C.

24. The process of claim 10 wherein said distribution of internal olefins prepared from the isomerization of a $C_{16}$ alpha olefin is, at equilibrium, equal to about 10% to about 30% at the 2 position, about 10% to about 20% at the 3 position, about 10% to about 20% at the 4 position, about 10% to 20% at the 5 position, about 5% to about 20% at the 6 position, about 5% to about 20% at the 7 position and about 2% to about 10% at the 8 position wherein said isomerization distribution is attained at 80% to 100% of the calculated isomer distribution.

25. The process of claim 10 wherein said disproportionation catalyst comprises at least one Group VIB metal supported on an inorganic oxide support.

26. The process of claim 25 wherein said inorganic oxide support has been treated with alkali or alkaline earth metal compounds.

27. The process of claim 10 wherein said disproportionation conditions include a temperature in the range of from about 100° C to about 150° C and a pressure in the range of from about 10 psig to about 250 psig.

28. The process of claim 10 wherein said separation in said second separation zone is performed under second separation conditions including a temperature in the range of from about 30° C to about 350° C and a pressure in the range of from about 1 psig to about 200 psig.

29. The process of claim 10 wherein said light olefin fraction produced in step (g) is recycled to said disproportionation of step (f) or said isomerization of step (e).

30. The process of claim 10 wherein said heavy olefin fraction separated in step (g) is recycled to said combined light and heavy alpha olefins in step (c) and passed to said purification-isomerization-disproportionation steps.

31. The process of claim 10 wherein said isomerization conditions include a temperature in the range of from about 100° C to about 150° C and a pressure in the range of from about 10 psig to about 250 psig.

32. The process of claim 10 wherein said unreacted ethylene in said first separation zone is recycled to said oligomerization of step (a).

* * * * *